United States Patent [19]

Nakata et al.

[11] Patent Number: 5,250,809
[45] Date of Patent: Oct. 5, 1993

[54] METHOD AND DEVICE FOR CHECKING JOINT OF ELECTRONIC COMPONENT

[75] Inventors: Shuji Nakata, 7-17, Honmachi 5-Chome, Toyonaka-Shi, Osaka-Fu; Minoru Nakamura, Osaka; Takeo Sakai, Kawagoe; Yoshimasa Shimizu, Kawagoe; Yoshihiro Kondo, Kawagoe, all of Japan

[73] Assignees: Shuji Nakata, Osaka; Denyo Kabushiki Kaisha, Tokyo, both of Japan

[21] Appl. No.: 824,081

[22] Filed: Jan. 22, 1992

[51] Int. Cl.[5] .............................................. G01N 25/72
[52] U.S. Cl. .................................... 250/330; 250/342; 250/358.1; 374/5; 374/124
[58] Field of Search ............ 250/341, 330, 342, 358.1; 374/5, 124, 137

[56] References Cited

U.S. PATENT DOCUMENTS

| | | | |
|---|---|---|---|
| 4,792,683 | 12/1988 | Chang et al. | 250/341 |
| 4,854,724 | 8/1989 | Adams et al. | 374/5 |
| 5,052,816 | 10/1991 | Nakamura et al. | 374/5 |

*Primary Examiner*—Carolyn E. Fields
*Attorney, Agent, or Firm*—Stevens, Davis, Miller & Mosher

[57] ABSTRACT

A method and device for checking a joint of an electronic component is arranged to apply heat energy to a joint containing a heat conductive material and receive the infrared ray radiated from said joint with an infrared camera. By processing the image information output from the infrared camera, the method and device can offer an area of a defect, an area ratio of a defect, pixel coordinates, a temperature distribution pattern, a distance between central axes of a particular portion of the joint, or a gradient angle. The obtained value is compared with a predetermined value for determining the kind of a defect and whether or not the joint is defective.

8 Claims, 16 Drawing Sheets

METHOD AND DEVICE FOR CHECKING JOINT OF ELECTRONIC COMPONENT

BACKGROUND OF THE INVENTION

1. Field of the Invention

The present invention relates to a method and a device for checking a joint formed in an electronic component, and more particularly to the method and the device which are capable of checking the joint of an electronic component based on the comparison of the information such as a form and a temperature distribution of a soldered portion regarded as a plane on an electronic circuit board.

2. Description of the Prior Art

It has been likely that the joints of an electronic component, in particular, the soldered portions on an electronic circuit board are often made defective. To overcome the occurrence of these defective soldered portions, various proposals for checking the joint have been made.

For example, there may be referred to as the technique of "Method and Device for Checking joint" disclosed in Japanese Patent Laid-Open No. 60-73347. The checking method and device take the steps of heating an object having a joint to be checked, measuring a radiation temperature of the heated portion from radiated infrared ray, and determining whether or not the joint is defective based on the measured result of the temperatures.

Concretely, it is measured how a temperature of the heated portion is changed for a short time. The atmosphere condition (surface condition of an object to be checked and others) of the object to be checked is measured on the basis of the temperature change for a short time to which the defective portion gives no influence. At a time, it is measured how a temperature of the heated portion is changed for a relatively long time. The change for a long time is influenced by the defective joint. Hence, it is determined whether or not the joint is defective on the basis of the the long time changed temperature amended on the atmosphere condition.

That is to say, this checking method uses the phenomenon that a normally soldered portion has so low heat resistance as not causing a large temperature rise but a incompletely soldered portion has so high heat resistance as causing a large temperature rise for checking the soldered joint. The foregoing prior art is improved in that the influence of the soldered surface state is considered for measuring the long time changed temperature.

As another prior art, there may be referred to as the technique of "Device for Checking Soldered Portion of Component mounted on Surface" disclosed in Japanese Patent Laid-Open No. 62-237346.

This device operates to heat the opposite surface to the actual component-mounted surface of an electronic circuit board, gauge a surface temperature of a soldered terminal component from the actual component-mounted surface, measure a temperature change of the soldered component after being heated for a constant time by a heater, and determining whether or not the soldered portion is defective.

FIG. 19 is a view showing the concept of this device. When a heater 104 heats a circuit board 101 from the rear side; a solder 103 is heated through a copper foil pattern 101a of the circuit board. A temperature measure unit 105 serves to measure the heat conductive state of the solder for a constant time from the start of heating. Based on this output, the determining unit 106 serves to determine whether or not the solder is defective.

The former prior art operates to measure the on-time change of a temperature of one spot of a joint and determine whether or not the joint is defective based on the temperature change. The latter prior art operates to measure the temperature distribution pattern on a line of the heated joint and determine whether or not the joint is defective based on the temperature distribution pattern.

The soldered joint of the electronic circuit board may include many defects such as bridge, solder ball, void, poor bond, blow hole, insufficient solder, lack of wetting and slippage of lead position. The on-time change of a temperature of one spot and the temperature distribution pattern of a line of a joint heated for a constant time offered by the foregoing prior arts make it possible to determine some kinds of the defects but impossible to determine all kinds of the defects and to generally determine the joint. Hence, the electronic circuit board checked by those prior arts may often become defective when it is built in the product.

SUMMARY OF THE INVENTION

It is, therefore, an object of the present invention to provide a method and a device for checking a joint of an electronic component which are capable of considering any kind of information such as form data or temperature data of a joint or a defect as a planar form and generally comparing and studying the information based on the planar form for the purpose of determining whether or not the soldered portion of a joint is defective.

In carrying out the object, the checking method according to the invention takes the steps of applying heat energy to a joint portion containing a heat conductive material, sensing an infrared ray radiated from the joint to be checked with an infrared camera, dividing and specifying the form of a defective portion of the joint on the basis of the image information sent from the infrared camera, generally analyzing the form information or the temperature information of the specified portion or the defective portion, and determining whether or not the defect occurs in the joint and the kind of the defect occurring in the joint.

The checking method and device according to the present invention operate to apply heat energy to the joint of an electronic component to be checked, sense the infrared ray radiated from the joint with the infrared camera, and process the image sent from the infrared camera. The processed image can extract all the defects of each joint as a surface form. Hence, all the defects can be checked. Further, the comparison and studying of a defective area, an area ratio, a border condition of a defect and a temperature distribution pattern result in being capable of properly determining whether or not the joint is defective and if it is, the kind of the defect.

BRIEF DESCRIPTION OF THE EMBODIMENT

In the following description the joint of an electronic component means a portion jointed by soldering, brazing, diffusion bonding (joint based on the diffusion of particles of both portions while a long-time contact, pressurizing and heating state remains), wirebonding (a kind of forge welding by hitting the heated tip of a slender metal lead to a small terminal when implementing the wiring inside of one IC chip), and bonding (joined by an adhesive agent).

Figure 1:
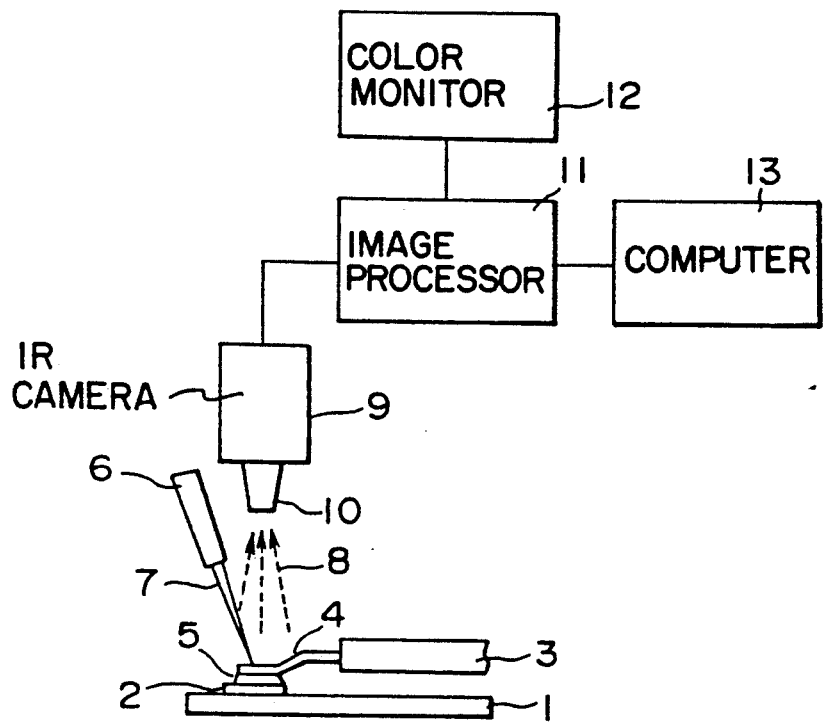
FIG. 1 is a view showing principle of the invention.

FIG. 1 is a view showing principle of the invention. As shown, 1 denotes a printed circuit board, 2 denotes a conductive pattern formed on the printed-circuit board 1, 3 denotes an electronic component, 4 denotes a lead, 5 denotes a soldered portion. The lead 4 of the electronic component 3 is joined to the conductive pattern through the soldered portion 5. 6 denotes a condensing unit and 2 denotes a laser beam. The laser beam 7 is applied from the condensing unit 6 to the joint of the electronic component formed on the printed-circuit board 1.

9 denotes an infrared camera, which serves to sense an infrared ray 8 radiated from a portion to be checked, that is, the printed-circuit board 1, the conductive pattern 2, the solder 5 and the lead 4. The radiation of the infrared ray 8 is expanded by an enlargement lens 10. 11 denotes an image processor, which serves to record or image-process the data about temperature distribution of the portion to be checked. Then, the thermal image is displayed on a color monitor 12. 13 denotes a computer, which serves to analyze the data about the temperature distribution, divide and specify each portion of joint or defect, and carry out comparison and collation of a form of each portion of joint or defect or temperature distribution for determining whether or not the joint is defective.

In turn, the description will be directed to the embodiment for image-processing a thermal image, dividing and specifying each portion of joint or defect, determining the kind of a defect of the soldered joint from the form and temperature information, and determining whether or not the joint is defective.

At first, the method for dividing and specifying each portion of joint from the thermal image will be described.

Figure 2:
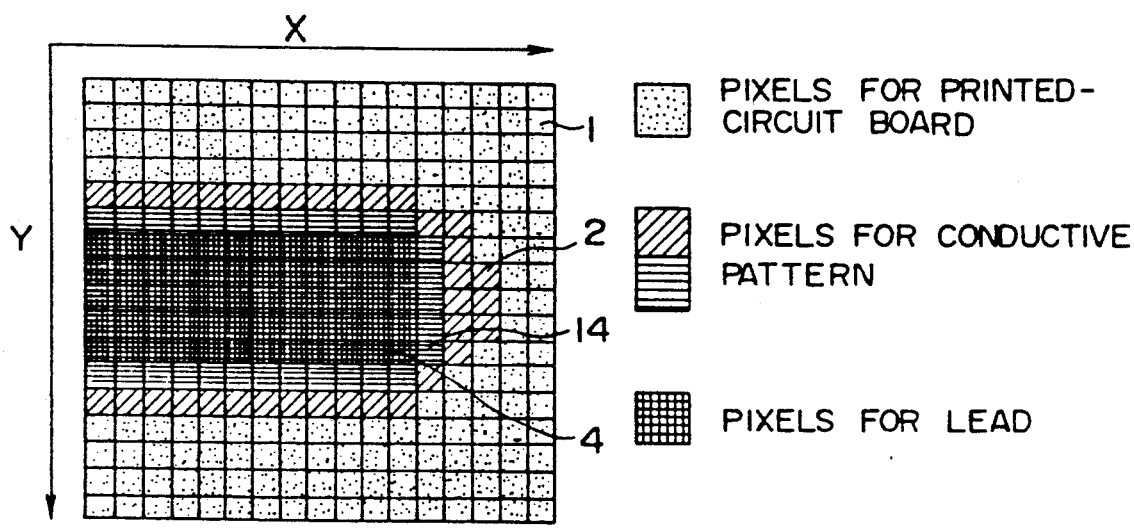
FIG. 2 is a schematic view showing a thermal image of a joint displayed on a color monitor.

FIG. 2 is a schematic view showing the thermal image of a joint displayed on the color monitor. This thermal image is picked up by applying a YAG laser beam to the lead of the integrated circuit element and heating it. The coordinates of the thermal image are composed of an X axis on the horizontal, a Y axis on the vertical, and a point of origin located at the upper left of the image.

In FIG. 2, like FIG. 1, 1 denotes the printedcircuit board, 2 denotes the conductive pattern and 4 denotes the lead. The lead has the highest temperature, the conductive pattern has the second, and the board has the third highest temperature. The conductive pattern contains a solder fillet 14 formed thereon.

The routine for dividing and specifying each portion of joint from the thermal image will be described.

Figure 3:
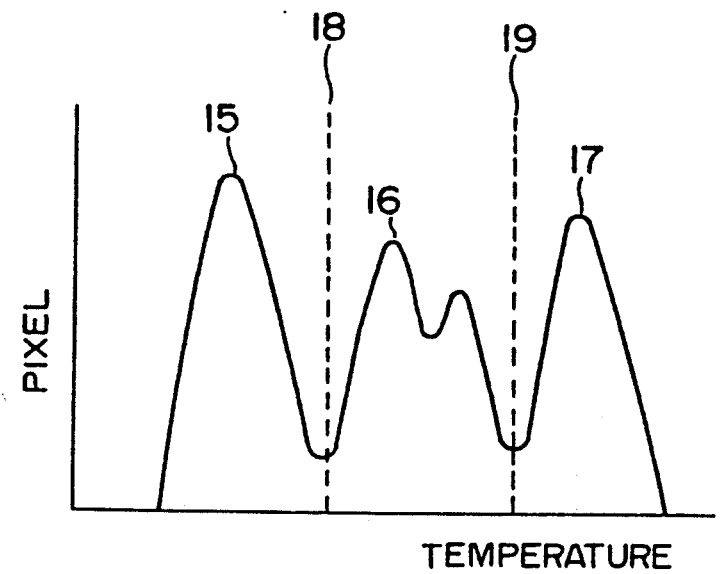
FIG. 3 is a graph showing temperature distribution of FIG. 2 as a histogram.

FIG. 3 is a graph showing the temperature distribution shown in FIG. 2 as a histogram form. As shown, 15 denotes a peak of the temperature distribution corresponding to the printed-circuit board, 16 denotes a peak corresponding to the conductive pattern, 17 denotes a peak corresponding to the lead, 18 denotes a temperature of a threshold value based on which the board and the conductive pattern are divided and specified, since the temperature indicating a valley bottom located between the respective peaks is the threshold value based on which the respective temperature regions are divided and specified. 19 denotes a temperature of a threshold value based on which the conductive pattern and the lead are divided and specified. For specifying the board, it is necessary to extract the coordinates of the pixels located in the temperature region of the threshold value 18 or less. For specifying the conductive pattern, it is necessary to extract the coordinates of the pixels in the temperature value of more than 18 to 19. Likewise, for specifying the lead, it is necessary to extract the coordinates of the pixels in the temperature region over 19.

Figure 4:
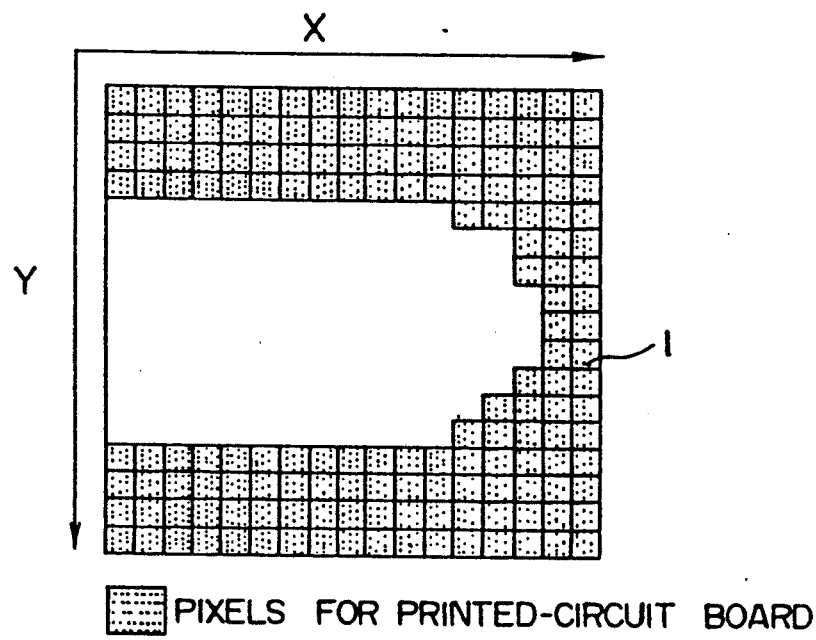
FIG. 4 is a schematic model view showing a thermal image for dividing and specifying a circuit board.

FIG. 4 is a schematic view showing a thermal image divided and specified by the above method. The thermal image shown in FIG. 4 indicates the case where the printed-circuit board 1 is divided and specified.

In turn, the description will be directed to the method for calculating an area of a defect of each divided and specified portion, determining the kind of the defect on the basis of the defect border condition, and determining whether or not the joint is defective.

At first, the description will be directed to an embodiment of the method for dividing and specifying a defect of each portion of joint from the thermal image, determining the kind of the defect from the condition of the defect border, and determining whether or not the joint is defective from the kind and the area of the defect or the area ratio of the defect.

Figure 5:
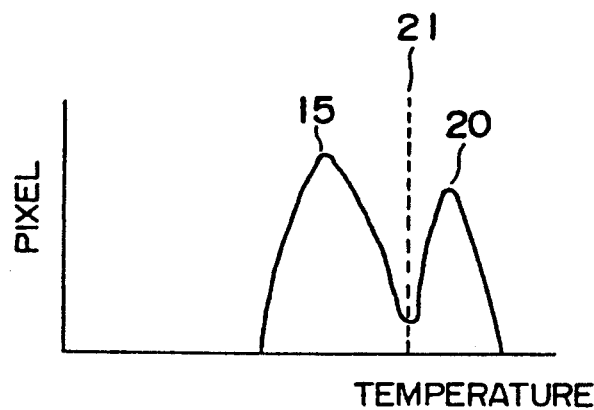
FIG. 5 is a graph showing the temperature distribution of the circuit board as a histogram.

FIG. 5 is a graph showing the temperature distribution of the printed-circuit board as a histogram. As shown, 15 denotes a peak for the printed-circuit board, 20 denotes a peak for the defect, 21 denotes a threshold temperature on which the board is divided from the defect and both are specified.

The defects existing in the printed-circuit board may include a bridge and a solder ball. Since the bridge comes into contact with the lead or the conductive pattern, the heat of the lead or the conductive pattern is conducted to the bridge, resulting in heating the bridge. Since the bridge has a small heat resistance, the bridge becomes higher in temperature than the printed-circuit board. The solder ball is heated by the conduction of the heat on the board. Hence, the temperature of the solder ball is lower than the board. However, since it is round and reflects the infrared ray radiated from the board, the actual temperature of the solder ball is represented as a higher temperature. By extracting the pixels composing the temperature region over the threshold temperature 21, it is possible to divide and specify the defect (bridge or solder ball).

The total area of the defect or the ratio of the defect to the object to be checked can be calculated from the number of the pixels for the defect or a ratio of a total number of the pixels composing the overall portion to be checked to the number of the pixels for the defect. Taking another way of looking at the ratio, this ratio indicates how the temperature distribution varies. If there exist many pixels having a higher temperature than the threshold value on which the defect is divided and specified, it means the variation of the temperature distribution is large. Hence, the standard deviation of the temperature distribution is used as an alternative characteristic of a ratio of a defective area to the total area.

The standard deviation s can be derived from the following equation:

$$s = \left[ (1/N) \sum_{i}^{m} \sum_{j}^{n} [T(X_i, Y_j) - T_m]^2 \right]^{\frac{1}{2}}$$

wherein Tm denotes an average value of a temperature, $$T_m = (1/N) \sum_{i}^{m} \sum_{j}^{n} T(X_i, Y_j), T(X_i, Y_j)$$

denotes the temperature of the pixel indicated by the coordinate (Xi, Yj), and N denotes the total number of pixels composing the portion to be checked.

Figure 6:
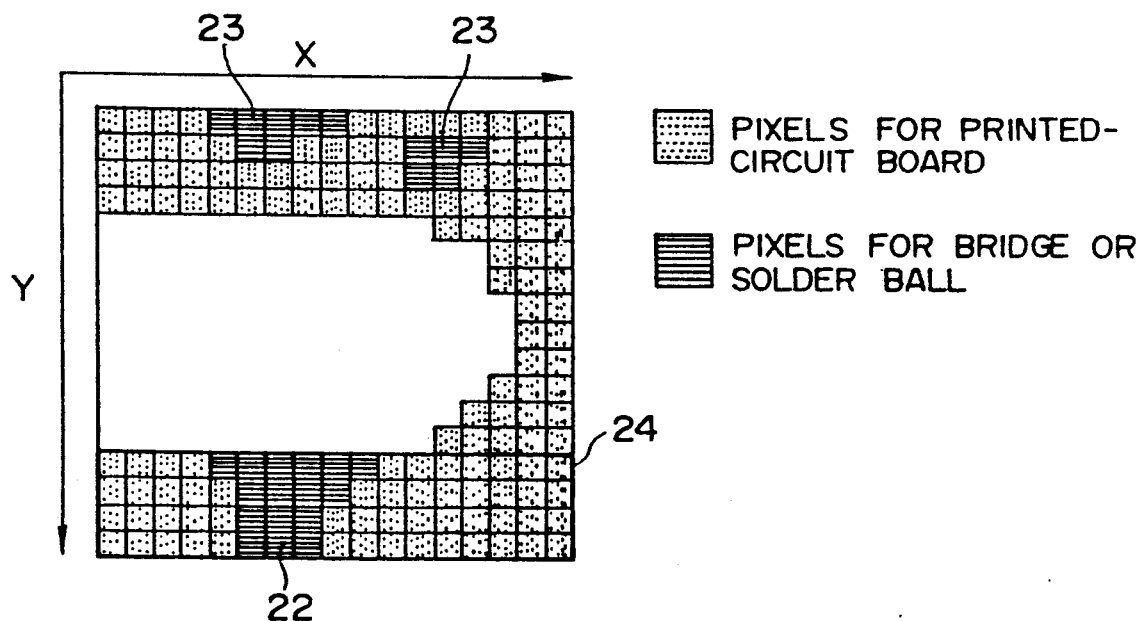
FIG. 6 is a view showing a thermal image of the circuit board on which a solder ball and a bridge are divided and specified.

FIG. 6 shows the thermal image of the printed-circuit board on which the bridge or the solder ball is divided and specified.

As shown, 22 denotes a bridge, 23 denotes a solder ball, and 24 denotes a frame of a window coming into contact with the conductive pattern and being set in the Y-axis direction.

In turn, the method for discriminating the bridge from the solder ball will be described.

Figure 7:
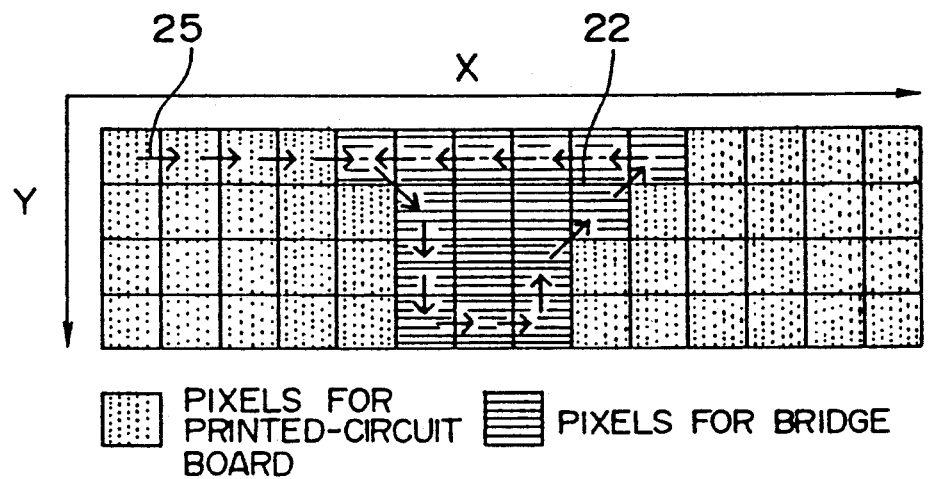
FIG. 7 is an expanded view of a part of the view shown in FIG. 6.

FIG. 7 shows the frame 24 of a window shown in FIG. 6. As shown, 22 denotes a bridge and 25 denotes an arrow indicating the scanning direction. As shown, the scanning is carried out along the X axis until the higher temperature than the threshold temperature 21 is sensed. The coordinate of the first pixel composing the temperature region over the threshold temperature 21 (FIG. 5) is memorized as a start point in memory.

Figure 8:
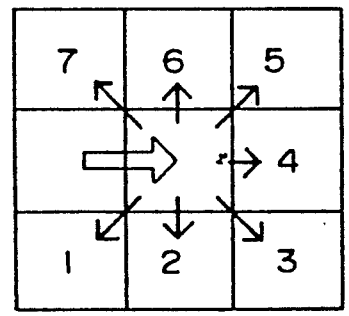
FIG. 8 is a view showing a priority sequence for scanning the thermal image shown in FIG. 7.

Next, the pixels having the temperature over the threshold value 21 are sensed along the priority shown in FIG. 8 and the coordinates of the sensed pixels are memorized in memory. After repeating the scanning, the scanning is returned to the start point, when the coordinates (Xdi, Ydj) to (Xdm, Ydn) of a contour line of a defect (bridge or solder ball) are defined.

The bridge is in the state where the adjacent conductive patterns are short-circuited by soldering. Hence, the bridge comes into contact with the conductive patterns and is required to extend at least to the end of the window. As a result, the condition for defining the bridge is:

$$Ydmax + 1 = Ypmin \text{ and } Ydmax - Ydmin > \alpha$$

or $$Ydmin - 1 = Ypmax \text{ and } Ydmax - Ydmin > \alpha$$

wherein Ydmax and Ydmin are a maximum value and a minimum value of the pixels composing a defect with respect to a Y axis, Ypmax and Ypmin are a maximum value and a minimum value of the pixels composing a conductive pattern with respect to a Y axis, and α denotes a predetermined value.

The foregoing procedure makes it possible to discriminate the bridge from the solder ball.

In turn, the description will be directed to an embodiment of the method for deriving an area of each defect.

In the foregoing method, the coordinates (Xdi, Ydj) to (Xdm, Ydn) of the contour of a defect are derived. Then, if the sum of each difference between the maximum value and the minimum value of the coordinates of an X axis is also derived, the area S of each defect can be obtained by the following expression:

$$S = \sum_{j}^{n} (Xd\text{max} - Xd\text{min} + 1)$$

wherein Xdmax and Xdmin denote a maximum value and a minimum value of each Ydj with respect to an X axis. By repeating this scanning on the board portion, it is possible to extract all the bridges or solder balls.

In case of extracting the bridge, the joint is determined to be defective, because the conductive pattern is short-circuited.

In case of extracting the solder ball, it is determined whether or not the joint is defective by comparing the total area of the solder ball, or an area ratio of said the total area of the solder ball to the total area of the board or the area of each solder ball to their respective predetermined values.

Next, the description will be directed to an embodiment of the method for dividing and specifying a defect of each joint portion, determining the kind of the defect from the temperature distribution pattern of the defect, and determining whether or not the joint is defective from the area of the defect or the ratio of the defective area to the total area of the board portion.

Figure 9:
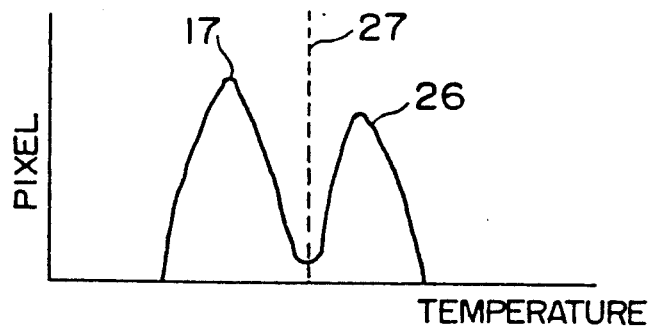
FIG. 9 is a graph showing temperature distribution of a lead portion as a histogram.

FIG. 9 is a graph showing the temperature distribution of the lead as a histogram form. As shown, 17 denotes a peak for the lead, 26 denotes a peak for the defect, and 27 denotes a threshold temperature on which the lead is divided from the defect and both are specified.

Since the defect serves as resistance to the heat conduction, the heat of the lead is prevented from being conducted to the conductive pattern, resulting in allowing the defective portion to be heated up to the higher temperature than the lead. By extracting the pixels composing the temperature region over the threshold temperature 27, therefore, it is possible to divide and specify the defect.

The use of the foregoing method makes it possible to derive the total area or the area ratio of the defects or the area of each defect.

Figure 10:
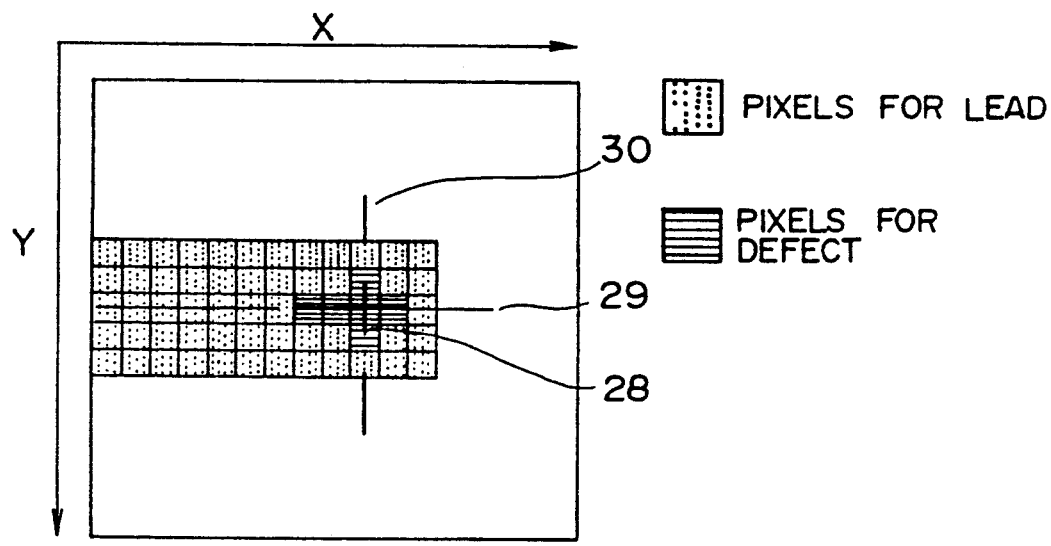
FIG. 10 is a view showing a thermal image of a lead portion where a defect is divided and specified.

FIG. 10 shows the thermal image of the lead on which the defect is divided and specified. As shown, 28 denotes a defect, 29 and 30 are a horizontal line (line extending in parallel to the central axis of the lead) and a vertical line (line extending vertically to the central axis of the lead) passing through the center of gravity of the defect portion.

The center of gravity and the central axis of the divided and specified area can be obtained by the following method.

From the coordinates of the pixels composing this area, it is possible to calculate the coordinate (Xg, Yg) of the gravity center and the gradient ($\theta$) of the major axis with respect to each pixel. For the calculation, the following expression will be used:

For the coordinate of the center of gravity, $$Xg = \sum_{i}^{m} Xi/N, \quad Yg = \sum_{j}^{n} Yj/N$$

For the gradient of the major axis, $$\theta = (\tfrac{1}{2}) \tan^{-1}[2Ixy/(Ix-Iy)]$$

wherein N denotes the total number of pixels composing the abovementioned area and Xi, Yj denotes the coordinates of the pixels composing the abovementioned area.

$$Ix = \sum_{i}^{m} (Xi - Yg)^2, \quad Iy = \sum_{j}^{n} (Yj - Yg)^2$$

$$Ixy = \sum_{i}^{m}\sum_{j}^{n} (Xi - Xg)(Yj - Yg)$$

The central axis can be obtained from the resulting coordinates of the center of gravity and the gradient of the major axis.

Figure 11A:
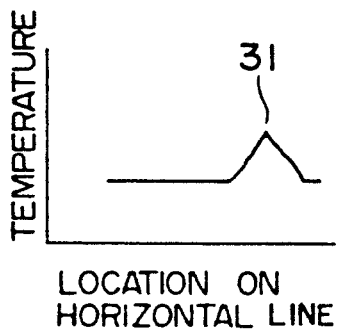
FIGS. 11A and 11B are graphs showing temperature distribution formed on a horizontal line and a vertical line passing through a center of gravity of a defect.
Figure 11B:
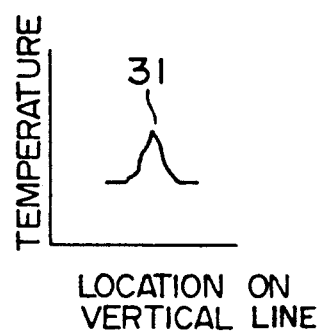

FIGS. 11A and 11B are graphs showing temperature distributions on the horizontal line 29 and the vertical line 30. As shown, 31 denotes a temperature distribution for a defect.

Then, by comparing the temperature distribution pattern on the horizontal and the vertical lines passing through the center of gravity of the defect with the temperature distribution pattern of the memorized internal defect, it is possible to determine the kind of the internal defect such as void, poor bond or blow hole. That is, the void portion indicates the distribution of a higher temperature than the poor bond portion. The poor bond portion indicates the distribution of a wider temperature than the void portion. Hence, the void portion and the poor bond portion are allowed to be easily determined. Since there exist many defects with small areas in case of the blow hole, the blow hole can be easily determined.

With respect to the void, the poor bond or the blow hole, by comparing the total area of the defects, the area ratio of the defects to the lead, the standard deviation of the temperature distribution of the lead or the area for each defect with their respective predetermined values, it is possible to determine whether or not the joint is defective.

In turn, the description will be directed to the routine for determining whether or not the solder is defective and the kind of the defect from the temperature information obtained from the divided and specified portion as a planar form.

The pixels composing the higher temperature region than the predetermined value are extracted within the area of the divided and specified conductive pattern.

Figure 12:
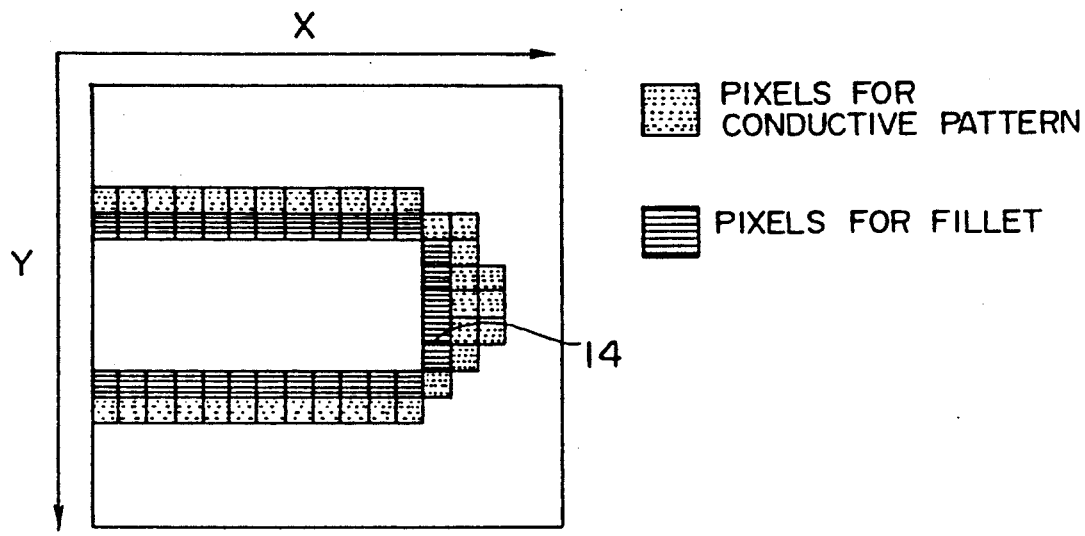
FIG. 12 is a view showing a thermal image of a divided and specified conductive pattern.

FIG. 12 shows the thermal image of the divided and specified conductive pattern. As shown, 14 denotes a higher temperature region than the predetermined value.

The temperature region 14 having a higher temperature than the conductive pattern surrounds the lead. This area 14 represents the smooth solder fillet formed around the lead. The solder fillet is inclined with respect to the observatory axis of the infrared camera and serves to reflect the infrared ray radiated around the fillet. As a result, the fillet is represented to have a higher temperature than the actual one.

In case that the number of the pixels composing the high temperature region exceeds the predetermined value, the sufficient fillet is formed. That is, it is considered that the portion is sufficiently wet. The portion is determined to be successful.

In case that the number of the pixels is equal to the predetermined value or less, the insufficient solder or the lack of wetting is considered. The portion is determined to be unsuccessful.

The insufficient solder results in making it substantially impossible to form the fillet, resulting in representing the thermal image where the board, the conductive pattern and the lead are represented in the simplest form. The surfaces of the lead and the conductive pattern are made to have a convex with a flat surface. Hence, the border of the temperature clearly appears for each portion. By comparing the temperature distribution graph with the standard temperature distribution graph, it is possible to easily determine the insufficient solder in the joint.

Figure 13:
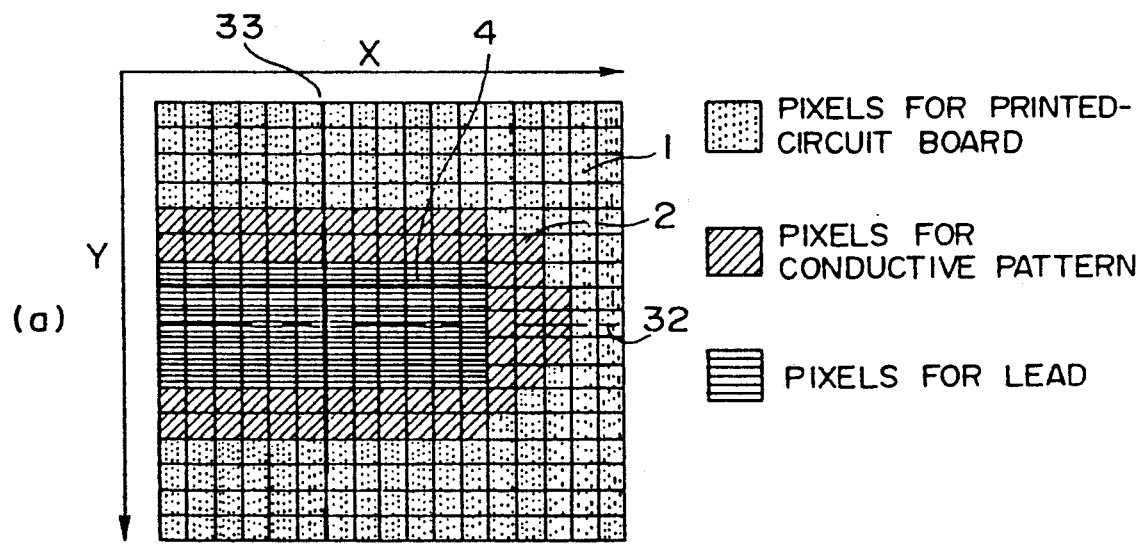
FIG. 13 is a view showing a thermal image appearing in case of insufficient solder.

FIG. 13 shows the thermal image formed in case of the insufficient solder. As shown, 1 denotes a printed-circuit board, 2 denotes a conductive pattern, 4 denotes a lead, 32 denotes a central axis of the lead, 33 denotes a vertical line perpendicular to the central axis 32 at the coordinates of the center of gravity of the lead.

Figure 14A:
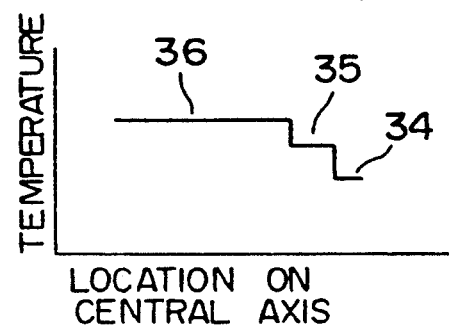
FIGS. 14A and 14B are graphs showing temperature distribution.
Figure 14B:
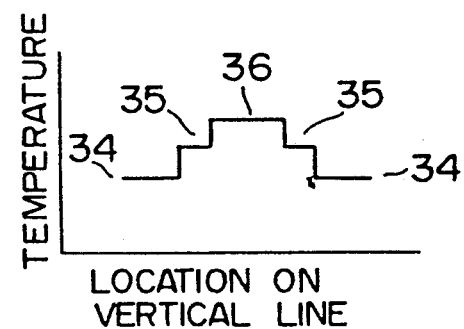

FIGS. 14A and 14B are graphs showing temperature distributions on the central axis and the vertical line. As shown, 34 denotes a temperature distribution for the board, 35 denotes a temperature distribution for the conductive pattern, and 36 denotes a temperature distribution for the lead. In both of the graphs, a quite simple stepwise form is represented.

The foregoing method has been implemented on the consideration that the area of the conductive pattern is generally observed. To check the area more accurately, the conductive pattern is divided into three areas. For each area, a window is provided. Then, the foregoing procedure is carried out for each window. It is possible to check the states of the fillets located at the three sides surrounding the lead.

Figure 15:
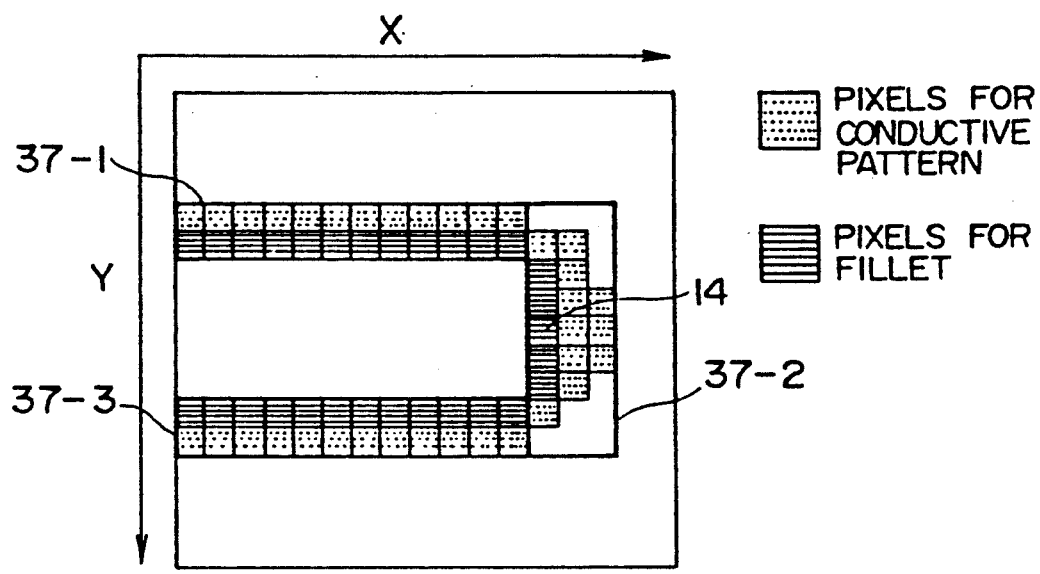
FIG. 15 is a view showing an example of a window set to the conductive pattern.

FIG. 15 shows an example of a window set for the conductive pattern. As shown, 14 denotes a temperature region over the predetermined value, 37-1, 37-2 and 37-3 are frames of the windows set to the three sides surrounding the lead.

In turn, the description will be directed to the routine for determining whether or not the solder is defective from the form information obtained from the divided and specified portion.

Figure 16:
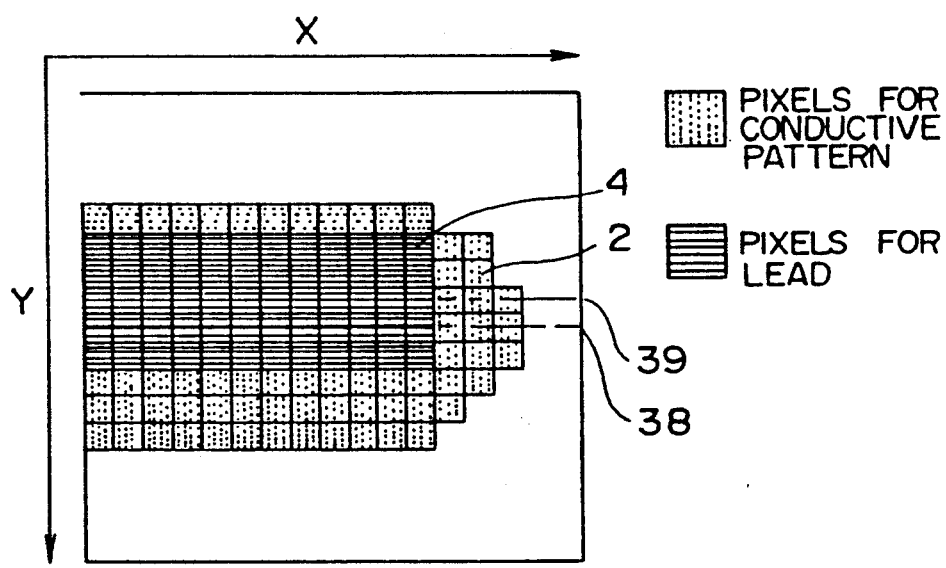
FIG. 16 is a view showing a thermal image of divided and specified conductive pattern and lead.
Figure 17A:
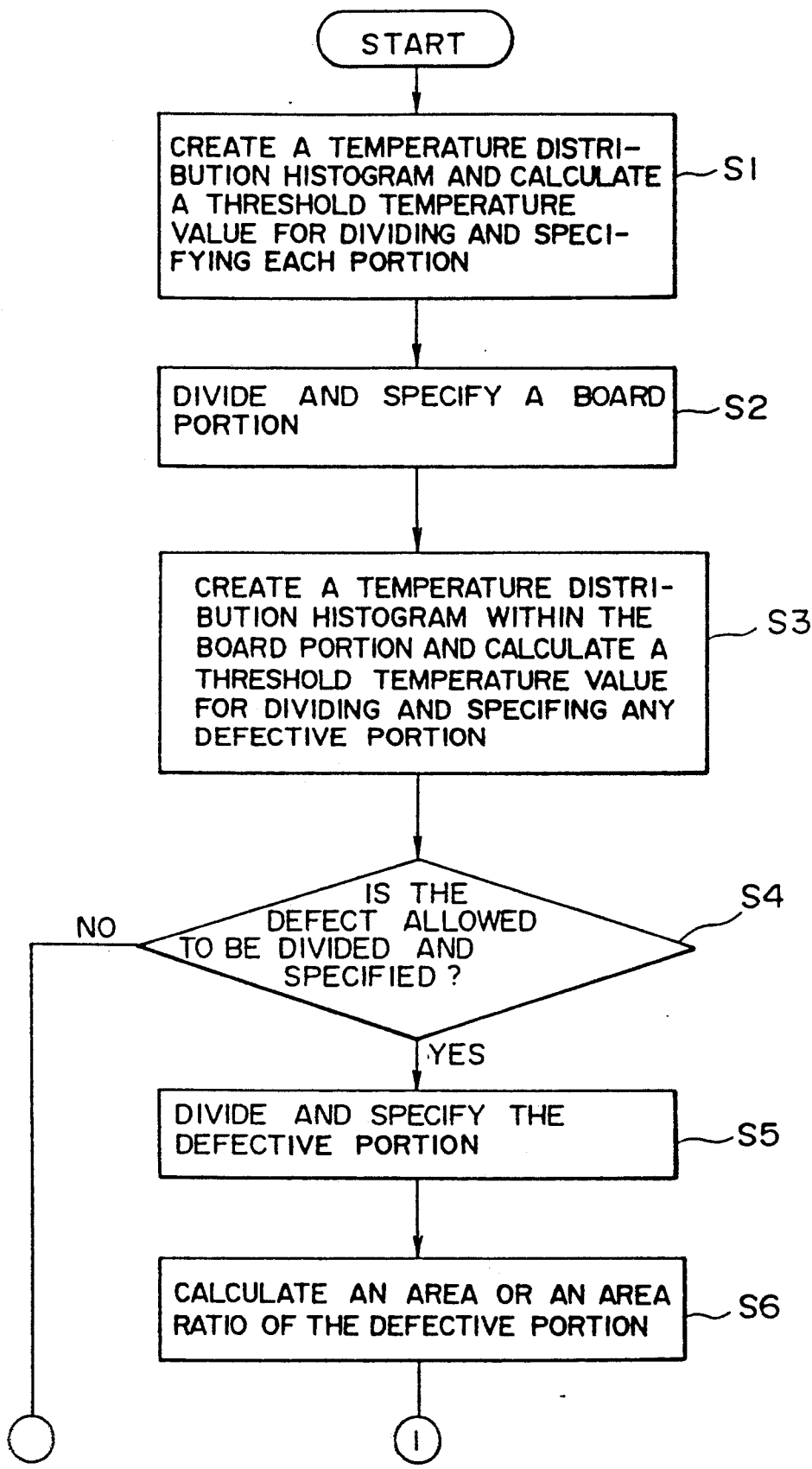
FIGS. 17A to 17F are flowcharts showing the checking method for a soldered joint.
Figure 17B:
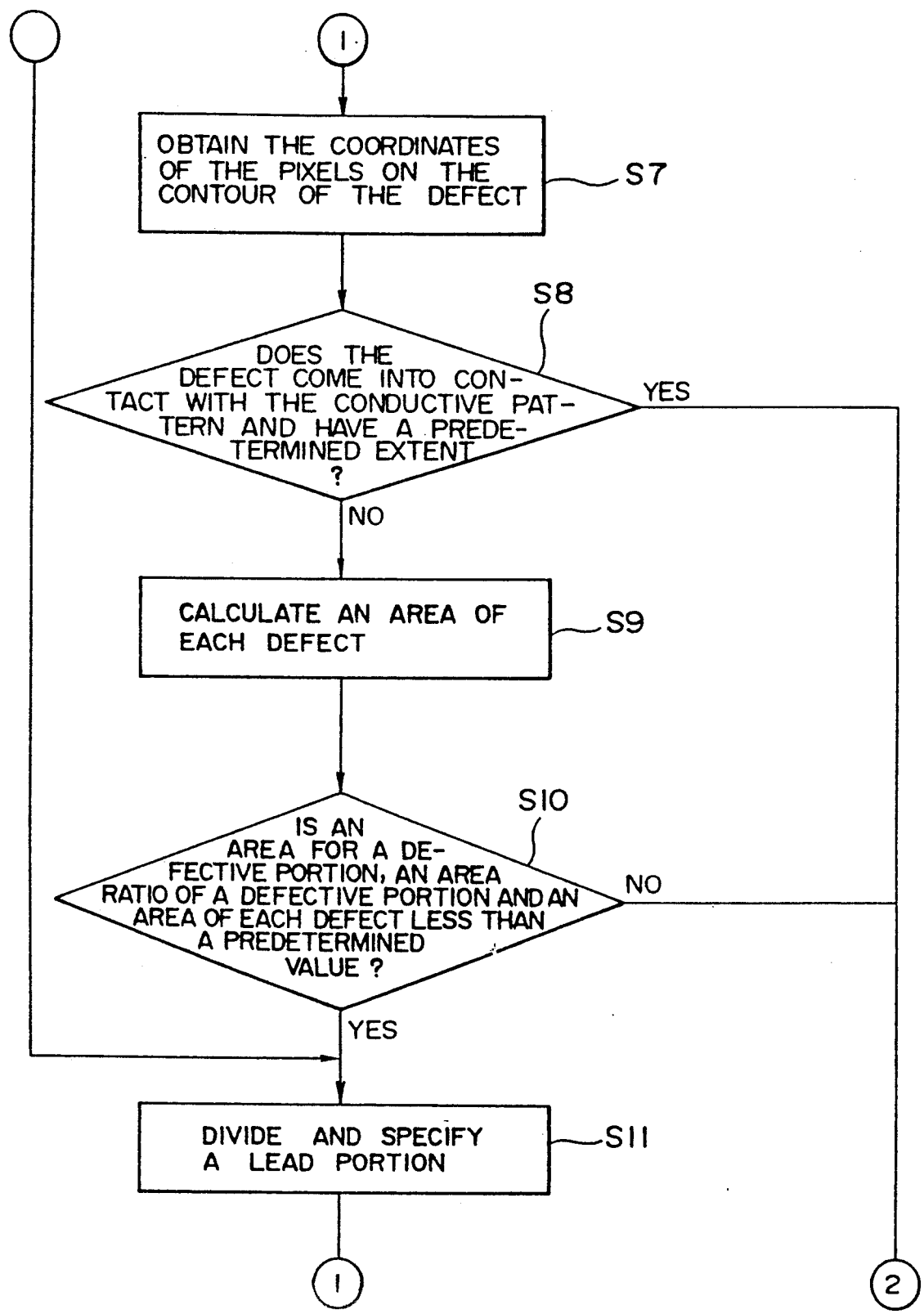
Figure 17C:
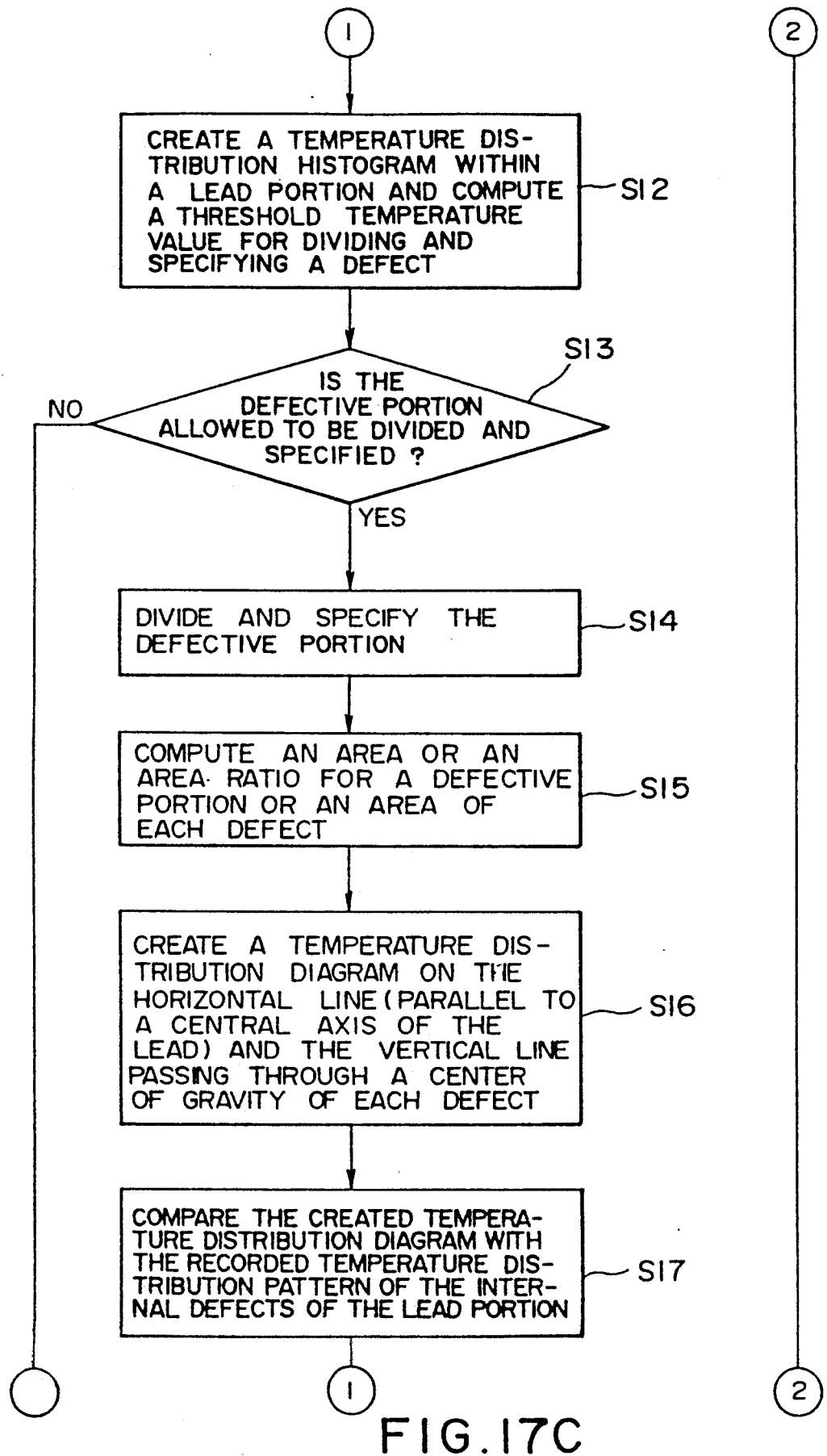
Figure 17D:
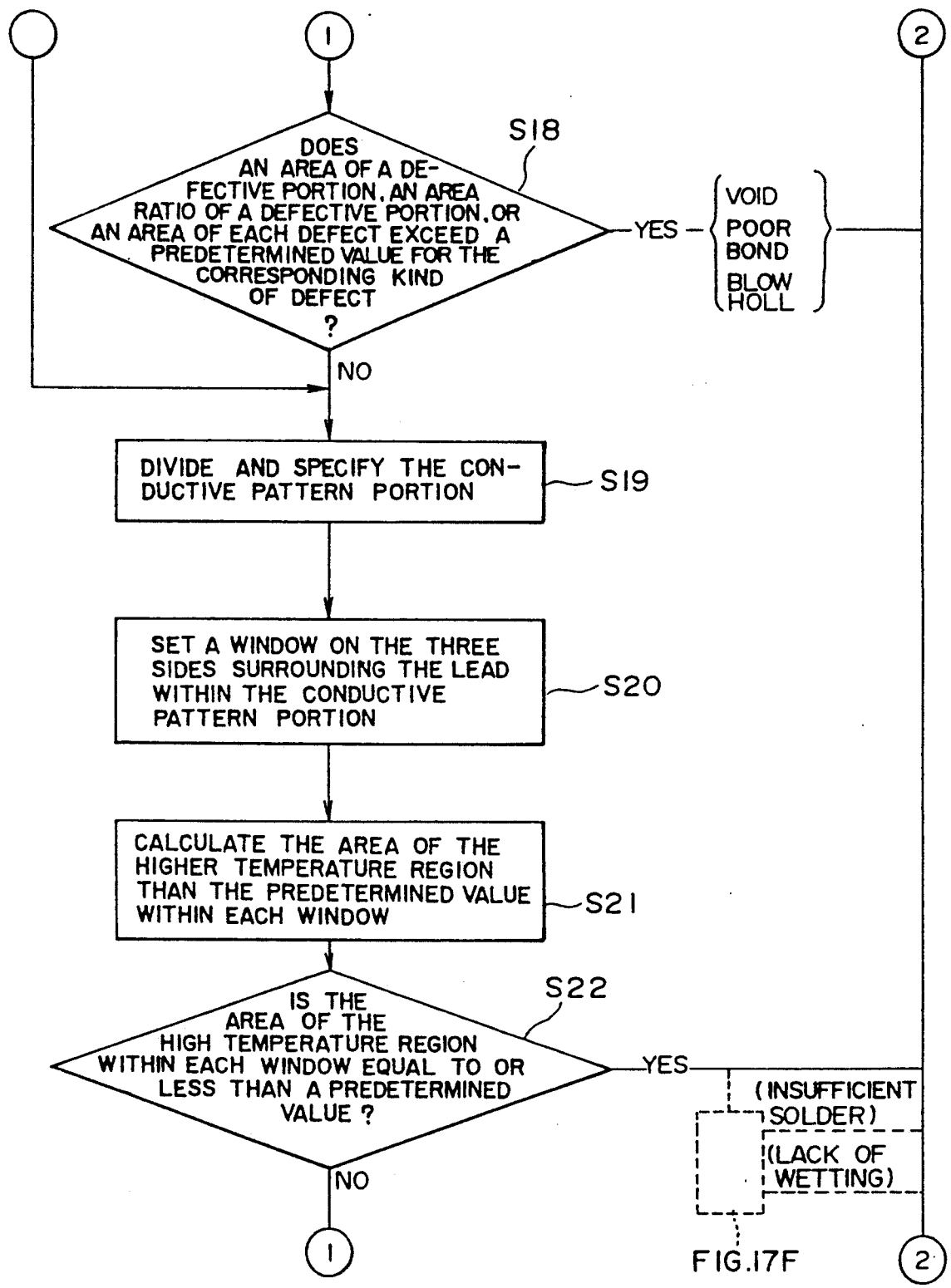
Figure 17E:
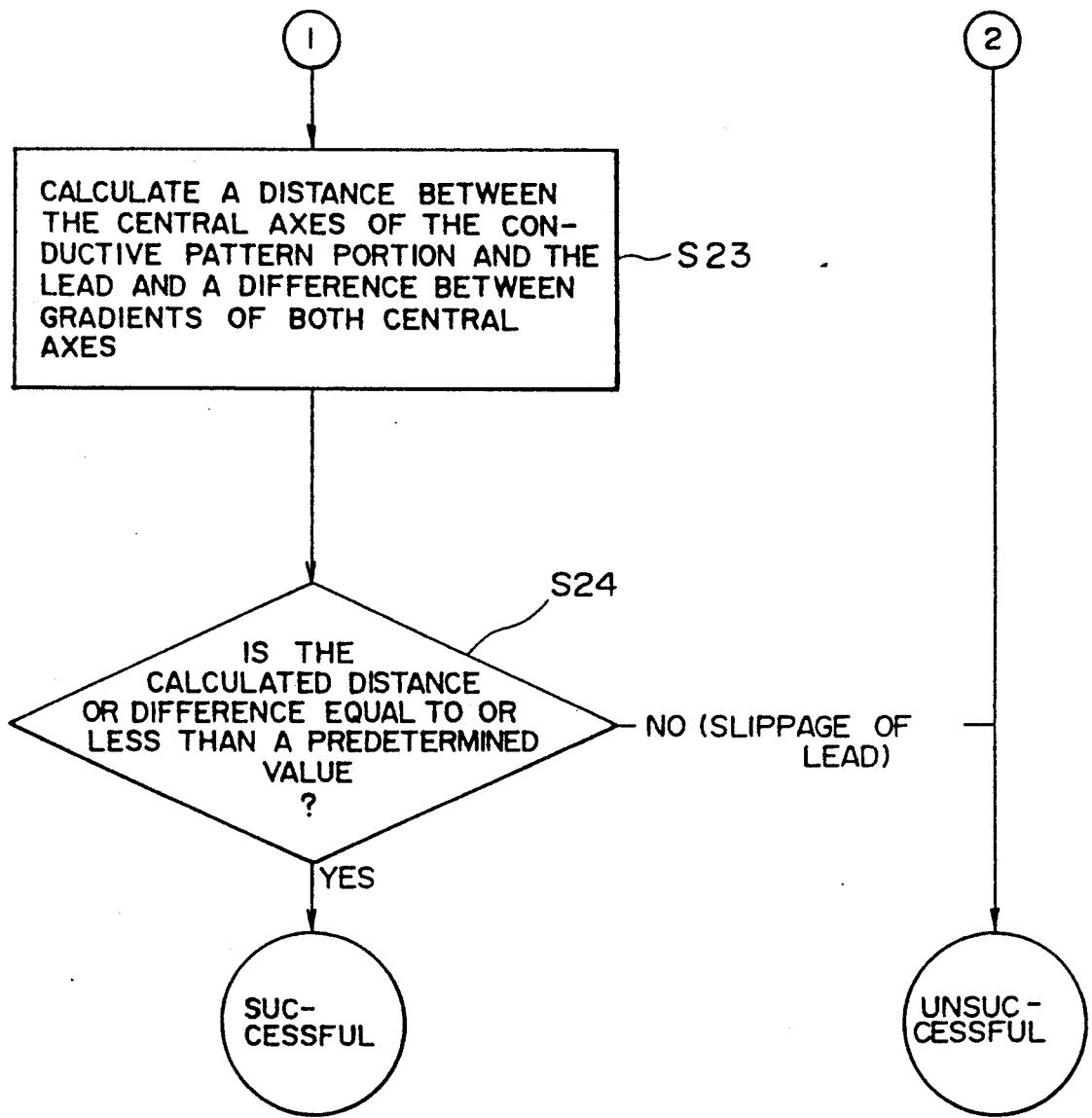
Figure 17F:
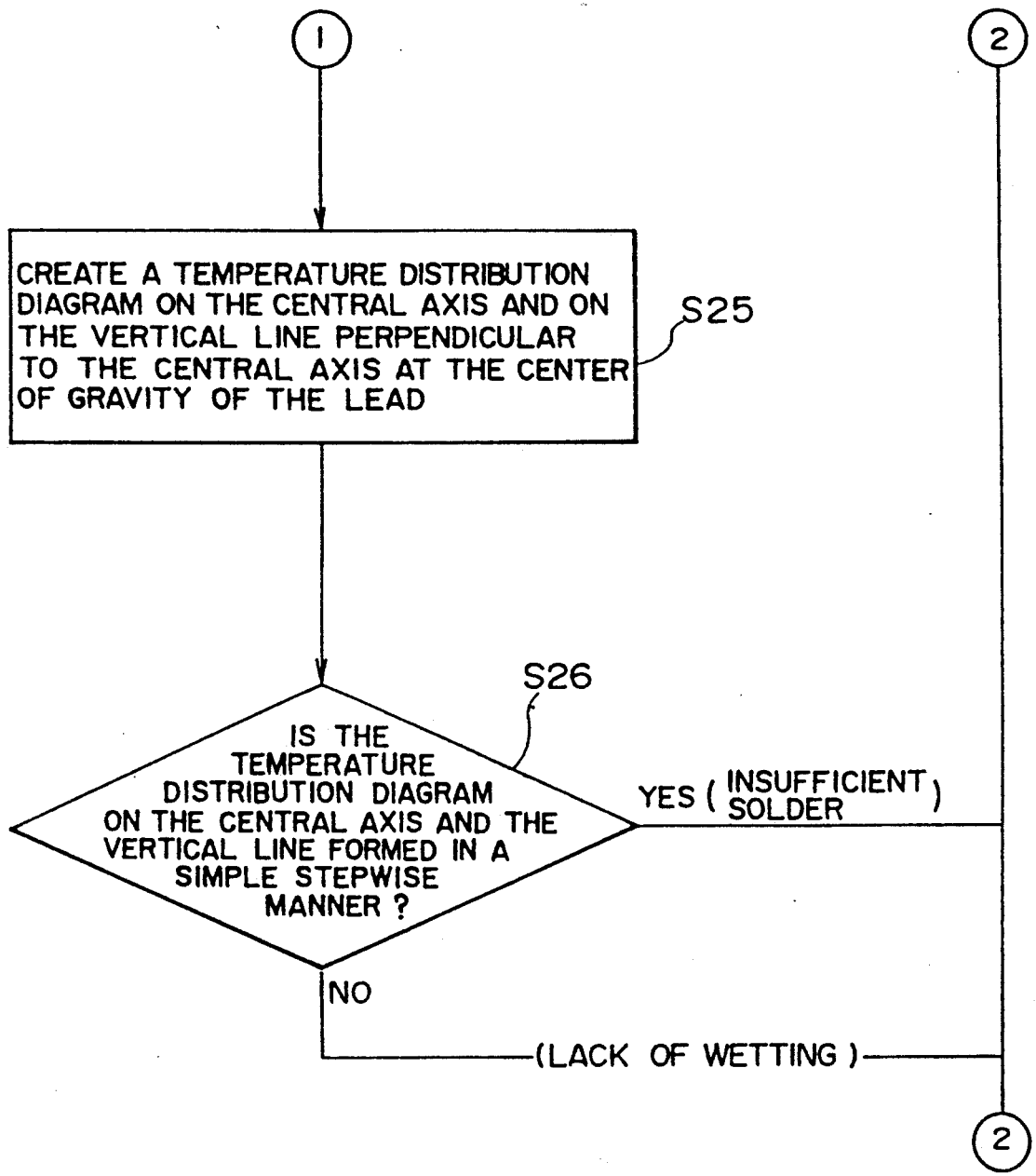

FIG. 16 shows the thermal image of the divided and specified conductive pattern and the lead. As shown, 2 denotes a conductive pattern, 4 denotes a lead, 38 denotes the central axis of the conductive pattern, and 39 denotes the central axis of the lead. In case that the distance (number of pixels) between the central axis 38 of the conductive pattern and the central axis 39 of the lead or the difference between the gradients of the central axes exceeds its own predetermined value, the slippage of the location of the lead is considered. Hence, the joint is determined to be unsuccessful.

The foregoing description has concerned with the routine for determining whether or not the joint is defective by means of analyzing the temperature information of each pixel within each area of the joints to be checked, calculating the total area of the defects existing in said area, the area ratio of the defects, the area of each defect, the standard deviation of the temperature distribution of each area, or the area having a higher temperature than the predetermined value, and comparing the calculated value with the predetermined value. Further, the foregoing description has also concerned with the routine for determining whether or not the joint is defective and the kind of the defect by comparing the border condition for the defective area with the predetermined condition or comparing the temperature distribution pattern of the defect with the predetermined value.

Moreover, the foregoing description has also concerned with the routine for determining whether or not the joint is defective by analyzing the form information of each pixel of each area of the joints to be checked in light of the plane, calculating the distance between the central axes or the difference between the gradients of the central axes, and comparing the calculated value with its corresponding predetermined value.

The foregoing routine is designed to analyze the temperature information about all the pixels of each area of the board, the lead and the conductive pattern, resulting in being able to generally analyze the state of the joint. To reduce the checking time, in place of all the pixels within each area of the board, the lead and the conductive pattern, it is possible to take a method of providing a particular window on part of each area, analyzing the temperature information about the pixels within the window, and determining whether or not the joint is defective. This method does not impair the feature of this invention which grasps the temperature information of the joint as a plane form and analyzes it.

In the foregoing embodiment, there has been employed a method for applying a YAG laser to the lead as a method for heating the joint. To obtain the accurate information with this method, the positioning accuracy of applying the laser beam is an important factor. Hence, the image of the object to be checked is taken by a CCD camera and the image is processed for obtaining the accurate positional relation between the object to be checked and the light condensing unit of the laser. In this case, when the image is processed, it is possible to sense the defects determined from outer appearances such as bridge, solder ball, insufficient solder, lack of wetting or slippage of lead.

To reduce the checking time, some or all of the defects identified from the outer appearances are determined from the image of the joint taken by the CCD camera and the internal defects such as void, poor bond and blow hole are determined from the processed thermal image. This method does not impair the feature of the invention which grasps the temperature information of the joint as a plane form and analyzes it.

The foregoing embodiment is arranged so that the heat energy is applied to the lead and is conducted from the lead to the solder, the conductive pattern and finally to the printed-circuit board.

Alternatively, it is possible to use the arrangement that the heat energy is applied to the board and is conducted from the board to the conductive pattern, the solder and finally to the lead.

Next, the description will be directed to a routine for checking the joint of an IC soldered on the printed-circuit board according to an embodiment of the invention.

FIGS. 17A to 17F are flowcharts showing a routine for checking the joint.

At a step S1, the temperature distribution about the joint to be checked is created as a histogram so as to calculate the threshold temperature for dividing and specifying each portion. At a step S2, the board portion on the thermal image is divided and specified according to the threshold temperature.

Proceeding to a step S3, the temperature distribution histogram is created within the board portion so as to calculate the threshold temperature for dividing and specifying the defective portion. Then, at a step S4, it is checked whether or not the defective portion is allowed to be divided and specified. In case that only one peak exists in the histogram of the temperature distribution and the defective portion cannot be divided and specified, the process goes to a step S11 at which "the lead portion is divided and specified." In case that the defective portion is allowed to be divided and specified, the defective portion is divided and specified at the step S5. Then, at a step S6, the area or the area ratio of the defective portion is derived.

Next, at a step S7, it is possible to obtain the coordinates of the pixels on the contour of the defect. At a step S8, it is checked whether or not the defect comes into contact with the conductive pattern and occupies a predetermined area. If yes, the defect is determined as a bridge and the joint is also determined as being unsuccessful. The conditions for determining the joint as being unsuccessful are:

$$Ydmax + 1 = Ypmin \text{ and } Ydmax - Ydmin > \alpha$$

or $$Ydmin - 1 = Ypmax \text{ and } Ydmax \; Ydmin > \alpha$$

wherein (Xdi, Ydj) to (Xdm, Ydn) correspond to the coordinates of the contour of each defect, Ydmax and Ydmin are a maximum value and a minimum value of the pixels composing the defect with respect to the Y axis, Ypmax and Ypmin are a maximum value and a minimum value of the pixels composing the conductive pattern with respect to the Y axis, and denotes $\alpha$ predetermined value.

If the defect does not come into contact with the conductive pattern or the predetermined area occupied by the defect is equal to the predetermined value or less, the defect is determined as a solder ball. With respect to the defect determined as a solder ball, at a step S9, the area of each solder ball is calculated from the coordinates of the contour.

That is to say, the coordinates (Xdi, Ydj) to (Xdm, Ydn) of the contour of each defect are derived. Then, the area S of each defect is calculated by the expression:

$$S = \sum_{j}^{n} (Xd\max - Xd\min + 1)$$

wherein Xdmax and Xdmin are a maximum value and a minimum value of each Ydj with respect to the X axis.

At a step S10, the area of the defective portion, the area ratio of the defective portion or the area of each defect is compared to its corresponding predetermined value. If the area or the area ratio of the defective portion exceed the respective predetermined values, the joint is determined as being unsuccessful.

Then, consider the joint which is less than the predetermined value and where the defect is not divided and specified within the board portion at the step S4. With respect to the joint, at a step S11, the lead portion is divided and specified. Next, at a step S12, the histogram of the temperature distribution is created within the area of the lead portion so as to calculate the threshold temperature at which the defective portion is divided and specified. At a step S13, it is checked whether or not the defective portion is divided and specified. In case that only one peak exists in the histogram of the temperature distribution and the defective portion is not divided and specified, the process goes to a step S19 at which "the conductive pattern is divided and specified." If the defective portion is allowed to be divided and specified, at the step S14, the defective portion is divided and specified. Then, at the step S15, the area or the area ratio of the defective portion or the area of each defect is calculated.

Proceeding to a step S16, the temperature distribution diagrams are created. The temperature distribution diagrams are located on the horizontal line and the vertical line passing through the center of gravity of each defect. The horizontal line corresponds to the parallel line to the central axis of the lead.

The horizontal and the vertical lines passing through the center of gravity of each defect can be derived as follows. At first, the central axis of the lead is obtained and then the parallel line to the central axis of the lead and the vertical line to the parallel line are drawn.

From the coordinates of the pixels composing the object to be checked, the coordinates (Xg, Yg) of the center of gravity and the gradient ($\theta$) of the major axis are calculated by the following expression: For the coordinates of the center of gravity, $$Xg = \sum_{i}^{m} Xi/N, Yg = \sum_{j}^{n} Yj/N$$

For the gradient of the major axis, $$\theta = (\tfrac{1}{2}) \tan^{-1}[2Ixy/(Ix - Iy)]$$

wherein N denotes a total number of the pixels composing the object to be checked and Xi, Yj denotes the coordinates of the pixels composing the object to be checked.

$$Ix = \sum_{i}^{m} (Xi - Yg)^2, \quad Iy = \sum_{j}^{n} (Yj - Yg)^2$$

$$Ixy = \sum_{i}^{m} \sum_{j}^{n} (Xi - Xg)(Yj - Yg)$$

From the calculated coordinates of the center of gravity and the gradient of its major axis, it is possible to obtain the central axis of the lead.

Next, compared with the temperature distribution pattern of the internal defects inside of the lead recorded at the step S17, it is possible to determine the internal defect such as void, poor bond or blow hole. At a step S18, the joint is determined as being unsuccessful if the area of the defective portion, the area ratio of the defective portion or the area of each defect exceeds the predetermined value of each kind of defect.

Consider the Joint which does not exceed the predetermined value and where the defect is not divided and specified within the lead area at the step S13. At a step S19, the conductive pattern is divided and specified. Next, at the step S20, a window is set to the three sides surrounding the lead within the conductive pattern area so as to calculate the area of the temperature region exceeding the predetermined value at the step S21. Next, at a step S22, if the high temperature region within each window has a predetermined value or less, the joint is determined as being unsuccessful because of insufficient solder or lack of wetting.

Then, consider the joint where the high temperature region within each window exceeds a predetermined value. At a step S23, the distance between the central axes of the conductive pattern and the lead or the difference between the gradients of both the central axes can be calculated.

Then, at a step S24, if the distance between the central axes or the difference between the gradients exceeds a predetermined value, the joint is determined as being unsuccessful because of the slippage of the lead. If it does not exceed the predetermined value, the joint is determined as being successful.

Consider the joint where the high temperature are within each window has a predetermined value or less at the step S22, at a step S25, the temperature distribution diagram is created on the central axis and of the vertical line perpendicular to the central axis of the lead at the center of gravity of the lead. Next, at a step S26, in case that the temperature distributions on the central axis and the vertical line are formed in a simple stepwise manner, the defective portion is determined as insufficient solder and if not, as lack of wetting.

The foregoing checking routine makes it possible to sense not only the apparent defects such as bridge, solder ball, insufficient solder, lack of wetting or slippage of lead but also the internal defects such as void, poor bond or blow hole and determine whether or not the joint is defective.

For determining the defects to be sensed from the outer appearance such as bridge, solder ball, insufficient solder, lack of wetting or slippage of lead, the checking routine can take an image of the joint with the CCD camera, process the image and analyze the defects. However, if the defects concern with the internal one such as void, poor bond or blow hole, it is necessary to analyze the thermal image.

Figure 18:
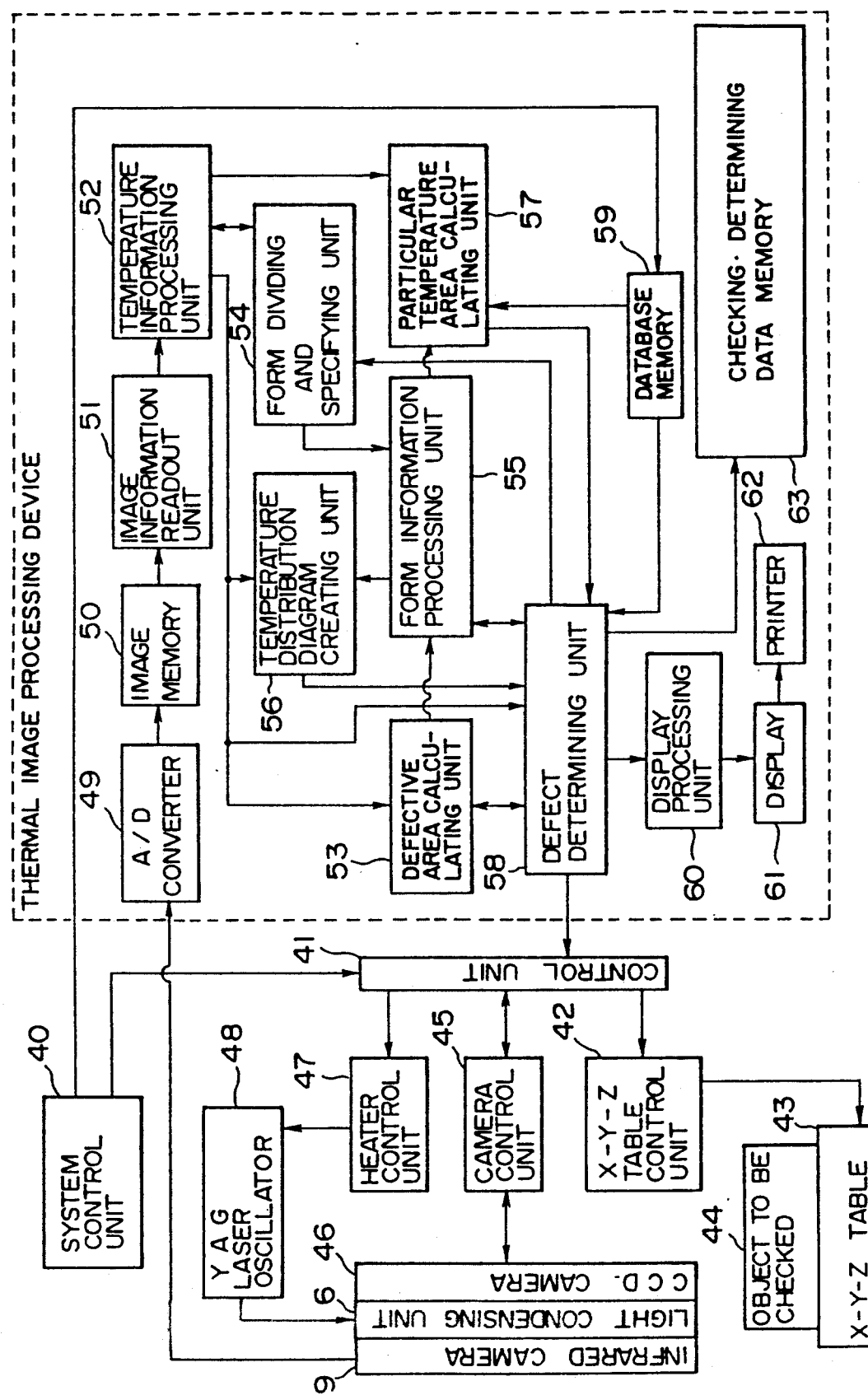
FIG. 18 is a block diagram showing arrangement of the checking device according to the invention.
Figure 19:
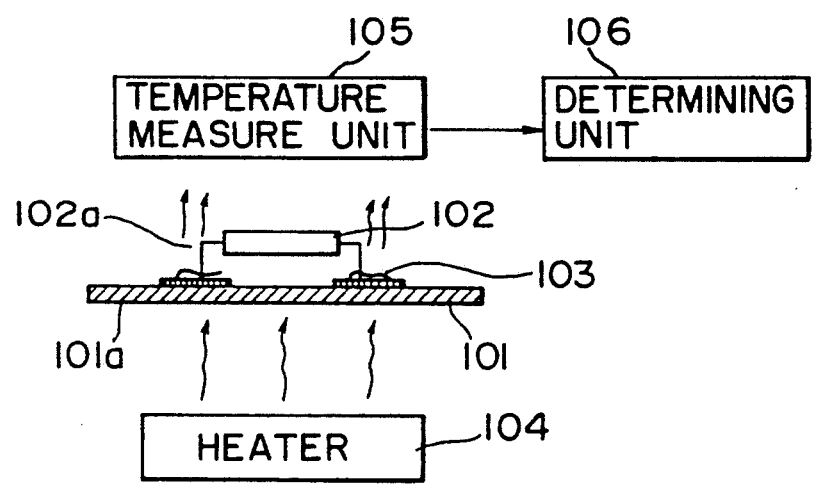
FIG. 19 is an explanatory view showing the conventional checking device for a soldered portion.

FIG. 18 is a block diagram showing the checking device according to an embodiment of the invention. As shown, the YAG laser is applied to the object to be checked for heating the object.

40 denotes a system control unit. An operator should input in the system control unit 40 the data such as locations of various components on the printed-circuit board, locations of joints and checking sequence and set the checking level in advance.

From a command from the system control unit 40, the control unit 41 performs the sequence control indicated below.

(1) The subject joint of the object to be mounted on an X-Y-Z table 43 through a X-Y-Z table control unit 42 therebetween is moved to a predetermined location based on the checking sequence input to the system control unit 40, where the first positioning (coarse movement) is carried out.

(2) The image of the joint is taken by a CCD camera 46 through a camera control unit 45. The location data is measured for doing the second positioning (minute movement).

(3) The laser is applied to the joint to be checked under the control of a heating control unit 47. The laser beam fired from a laser oscillator 48 is applied to the joint to be checked through a light condensing unit 6. In synchronization with the application of the laser, the thermal image is taken. The infrared ray radiated from the joint to be checked is received by an infrared camera 9 and is output as an analog thermal image signal. The analog thermal image signal is converted into a digital amount in an analog-to-digital converter 49. The converted signal is memorized at a predetermined address of an image memory 50. The thermal image signal memorized in the image memory 50 is processed by the following routine. The processing of the thermal image signal results in being able to determine whether or not the joint is defective.

51 denotes an image information readout unit, which serves to read out a thermal signal memorized in the image memory 50.

52 denotes a temperature information processing unit, which serves to create a histogram of temperature distribution of the pixels composing each portion of the joint and calculate a threshold temperature for dividing and specifying each portion of the joint. 54 denotes a form dividing and specifying unit, which serves to divide and specify each portion of the joint based on the threshold temperature.

The temperature information processing unit 52 serves to create the histogram of the temperature distribution of each of the pixels composing each divided and specified portion and calculate the threshold temperature for dividing and specifying the defective portion. The defective area calculating unit 53 serves to calculate the area or the area ratio of the defective portion depending on the threshold temperature. 58 denotes a defect determining unit, which serves to compare the area or the area ratio of the defective portion with the predetermined value memorized in a database memory 59 selected at the checking level set in the system control unit 40 and determine whether or not the joint is defective according to the compared result.

In this case, the temperature information processing unit 52 serves to calculate the threshold temperature for dividing and specifying the defective portion. The defective area calculating unit 53 serves to calculate the area of the defective portion. As an alternative method, the temperature information processing unit 52 calculates the threshold value and the form dividing and specifying unit serves to divide and specify the defective portion. Next, the defective area calculating unit 53 calculates the area of the defective portion.

The form dividing and specifying unit 54 serves to divide and specify the defective portion and the form information processing unit 55 serves to obtain the coordinates of the pixels on the contour of the defect. The defect determining unit 58 serves to determine the defect on the basis of the expression memorized in the database memory 59 for determining whether or not the joint is successful. Next, the defective area calculating unit 53 serves to calculate the area of each defect and the defect determining unit 58 serves to compare the calculated area with the predetermined value memorized in the database memory 59 selected on the checking level set in the system control unit 40 for determining whether or not the joint is defective.

The form information processing unit 55 further obtains the horizontal line and the vertical line passing through the center of gravity of each defect divided and specified by the form dividing and specifying unit 54. The temperature distribution diagram creating unit 56 then creates a temperature distribution diagram on the horizontal line and the vertical line, based on the temperature information sent from the temperature information processing unit 52. The defect determining unit 58 serves to compare the temperature distribution diagram with the temperature distribution diagram memorized in the database memory 59 for determining the kind of each defect. The determined defect is compared with the predetermined value for each kind of defect memorized in the database memory 59 selected on the basis of the checking level set by the system control unit 40 for determining whether or not the joint is defective.

The form information processing unit 55 serves to set a predetermined window within the area of each portion divided and specified by the form dividing and specifying unit 54 if necessary. The particular temperature area calculating unit 57 calculates within the set window the area of the temperature region which exceeds the predetermined value of a particular temperature memorized in the database memory 59 selected on the checking level set in the system control unit 40. The defect determining unit 58 then compares the calculated area with the predetermined value of the area of the high temperature region memorized in the database memory 59 selected on the checking level set in the system control unit 40 for the purpose of determining whether or not the joint is defective.

If the joint is determined to be defective, the form information processing unit 55 serves to set a particular line within a window. The temperature distribution diagram creating unit 56 creates a temperature distribution diagram on the particular line based on the temperature information sent from the temperature information processing unit 52. In the defect determining unit 58 the created temperature distribution diagram is compared with the temperature distribution pattern memorized in the database memory 59 for the purpose of determining the kind of a defect.

The form information processing unit 55 serves to calculate the distance between the central axes of respective portions or the difference between the gradients of the central axes of respective portions divided and specified in the form dividing and specifying unit 54 if necessary. The defect determining unit 58 compares the calculated distance or difference with the predetermined value memorized in the database memory 59 selected on the checking level set in the system control unit 40 for determining whether or not the portion of the joint is defective.

The display processing unit 60 serves to process the thermal image signal and the additional information and provide them to the display 61 for displaying the necessary information at a predetermined color and format.

62 denotes a printer, which serves to print out information if necessary.

63 denotes a memory for the checking data and determining data. The checking determining data memory unit 63 serves to memorize the determined state and the determined result of the defect determining unit 58. The data memorized therein is used for modifying the database.

Upon completion of checking one joint, the control unit 41 repeats the foregoing sequence control based on the checking sequence input to the system control unit 40. That is to say, the first positioning (coarse movement) is carried out for the next joint of the object to be checked 44 mounted on the X-Y-Z table 43 under the control of the X-Y-Z table control unit 42. The foregoing process is repeated in a similar manner.

The foregoing routine is designed to sense the defects identified from their outer appearances such as bridge, solder ball, insufficient solder, lack of wetting or slippage of lead. However, for the defects identified from the outer appearances, the image of the section of the joint is taken with the CCD camera. The image signal is processed and analyzed for sensing the defect and determining whether or the joint is defective.

That is, after doing the first positioning of the object to be checked under the control of the X-Y-Z control unit, the second positioning is carried out with the CCD camera. At a time, the defects identified from their outer appearances are allowed to be found out from the image. If they are found out, the checking of the joint based on the thermal image is left out. Then, the checking process goes to the next joint for reducing the checking time. However, for the internal defects such as void, poor bond or blow hole, the thermal image signal is processed for dividing and specifying the form of a defect and the kind of the defect is determined. Next, the area or the area ratio of a defective portion or the area of each defect is calculated and the calculated area is compared to the predetermined value for each kind of defect. Based on the compared result, it is possible to determine whether or not the joint portion is defective.

The foregoing embodiment has been concretely described with reference to the drawings. The embodiment does not limit the present invention.

As described above, unlike the prior arts, the present invention is arranged to sense all the defects from the temperature information of the pixels composing the portion of the joint, generally analyze the area of each defect, the temperature distribution or the form information, identify the kind of the defect, and determine whether or not the solder of the joint is defective by referring to the predetermined value for each kind of defect, without having to determine whether or not the joint is defective from the on-time change of a temperature at one place or the temperature distribution pattern on the line after heating the joint for a certain time. That is to say, the invention makes it possible to sense all the possible defects in the soldered joint of an electronic component and determine whether or not the joint is defective.

When the printed-circuit board checked by the present invention is built in the product, no failure resulting from the defective solder takes place in the product.

The present invention is capable of dividing and specifying the form of each portion of the joint, sensing the defect occurring in each portion, and determining whether or not the joint is defective. Hence, it is possible to check the defects identified from the outer appearances and the internal defects at the respective steps, resulting in reducing the checking time and enhancing the reliability of the checking.

Since the kind of the defect is allowed to be identified, the identified result can be fed back to the soldering step. It results in improving the soldering step and preventing the occurrence of the defects.

What is claimed is:

1. In a device for checking a joint of an electronic component having means for applying heat energy to a joint portion containing a heat conductive material, means for receiving the infrared rays radiated from said joint portion with an infrared ray camera, said device comprising:

means for memorizing an output signal of said infrared camera as image information;

means for calculating a threshold temperature value for dividing and specifying a defect, based on said memorized image information;

means for dividing and specifying said defect depending on said threshold temperature value;

means for obtaining the coordinates of pixels corresponding to a contour of the divided and specified area of said defect;

means for calculating an area or an area ratio of said divided defective portion, based on said threshold temperature value or calculating an area of each defect from said coordinates of the pixels;

means for comparing said area or area ratio or area of each defect with a corresponding predetermined value recorded in the database, for determining whether or not the joining state of said joint is defective.

2. A checking device according to claim 1, wherein said coordinates of the pixels corresponding to the contour of each defect obtained by said obtaining means are compared with the predetermined conditions recorded in the database for determining the kind of a defect and whether or not the joining state of said joint is defective.

3. A checking device according to claim 1 further comprising means for creating a temperature distribution diagram on a particular line about said defect, and wherein said temperature distribution diagram is compared with a predetermined temperature distribution pattern memorized in the database, for determining the kind of said defect and whether or not the joining state of said joint is defective.

4. In a device for checking a joint of an electronic component having means for applying heat energy to a joint portion containing a heat conductive material, means for receiving the infrared rays radiated from said joint portion with an infrared ray camera, said device comprising:

means for memorizing an output signal of said infrared camera as image information;

means for calculating a standard deviation of a temperature distribution about each.. portion of said joint, based on said image information; and means for comparing said standard deviation with a predetermined value memorized in a database for determining the kind of defect and whether or not the joining state of said joint is defective.

5. In a device for checking a joint of an electronic component having means for applying heat energy to a joint portion containing a heat conductive material, means for receiving the infrared rays radiated from said joint portion with an infrared ray camera, said device comprising:

means for memorizing an output signal of said infrared camera as image information;

means for calculating a threshold temperature value for dividing and specifying each portion of said joint;

means for dividing and specifying a predetermined portion depending on said threshold temperature value;

means for setting a predetermined window to said specified portion;

means for calculating an area of a temperature region having at least a predetermined temperature memorized in a database; and means for comparing said area with a predetermined value memorized in the database, for determining the kind of defect and whether or not the joining state of said joint is defective.

6. A checking device according to claim 5, further comprising means for creating a temperature distribution diagram on a particular line and wherein said temperature distribution diagram is compared with a predetermined temperature distribution pattern memorized in the database for determining the kind of said defect and whether or not the joining state of said joint is defective.

7. In a device for checking a joint of an electronic component having means for applying heat energy to a joint portion containing a heat conductive material, means/ for receiving the infrared rays radiated from said joint portion with an infrared ray camera, said device comprising:

means for memorizing an output signal of said infrared camera as image information;

means for calculating a threshold temperature value for dividing and specifying a portion of said joint;

means for dividing and specifying a predetermined portion depending on said threshold temperature value;

means for calculating a distance between central axes of said specified portions or a difference between gradients of said central axes; and means for comparing said calculated distance or difference with the corresponding predetermined value memorized in a database for determining whether or not the joining state of said joint is defective.

8. In a method for checking a joint of an electronic component having the steps of applying het energy to a joint portion containing a heat conductive material, receiving the infrared rays radiated from said joint portion with an infrared camera, and checking whether or not said joint is defective, said method comprising the steps of:

deriving a standard deviation in temperature distribution, based on the image information output from said infrared camera;

comparing said standard deviation in temperature distribution with a predetermined value; and determining whether or not the joining state of said joint is defective, based on the compared result.

* * * * *